United States Patent
Minakata et al.

(10) Patent No.: US 12,350,053 B2
(45) Date of Patent: Jul. 8, 2025

(54) ELECTRODE AND BIOSENSOR

(71) Applicant: Nitto Denko Corporation, Ibaraki (JP)

(72) Inventors: Masayuki Minakata, Ibaraki (JP); Ryoma Yoshioka, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 833 days.

(21) Appl. No.: 17/436,583

(22) PCT Filed: Mar. 2, 2020

(86) PCT No.: PCT/JP2020/008643
§ 371 (c)(1),
(2) Date: Sep. 3, 2021

(87) PCT Pub. No.: WO2020/184249
PCT Pub. Date: Sep. 17, 2020

(65) Prior Publication Data
US 2022/0142540 A1    May 12, 2022

(30) Foreign Application Priority Data
Mar. 8, 2019    (JP) ................. 2019-042985

(51) Int. Cl.
*A61B 5/257*    (2021.01)
*A61B 5/00*    (2006.01)

(52) U.S. Cl.
CPC ............ *A61B 5/257* (2021.01); *A61B 5/6833* (2013.01)

(58) Field of Classification Search
CPC .............. A61B 5/257; A61B 5/6833; A61B 2562/125; A61B 5/259; A61B 5/268
See application file for complete search history.

(56) References Cited

U.S. PATENT DOCUMENTS

| | | |
|---|---|---|
| 5,385,679 A | 1/1995 | Uy et al. |
| 5,536,446 A | 7/1996 | Uy et al. |
| 2003/0224160 A1 | 12/2003 | Murakami et al. |
| 2013/0284244 A1 | 10/2013 | Kato et al. |
| 2014/0303470 A1 | 10/2014 | Tsukada et al. |

(Continued)

FOREIGN PATENT DOCUMENTS

| | | |
|---|---|---|
| CN | 103229251 A | 7/2013 |
| CN | 104673123 A | 6/2015 |

(Continued)

OTHER PUBLICATIONS

Official Communication Pursuant to Article 94(3) EPC dated Jan. 11, 2024 for corresponding European Patent Application No. 20 769 578.4 (6 pages).

(Continued)

*Primary Examiner* — Tse W Chen
*Assistant Examiner* — Joseph A Tombers
(74) *Attorney, Agent, or Firm* — Hauptman Ham, LLP

(57) ABSTRACT

An electrode according to the present invention contains a conductive polymer; a binder resin; and a plasticizing agent, wherein the electrode has a plate shape having a pair of principal surfaces parallel to each other, and wherein a ratio of a content of the plasticizing agent to a content of the conductive polymer being 0.5 to 500.0 in a surface part of the electrode located at less than or equal to 1 μm from a surface of the electrode.

5 Claims, 6 Drawing Sheets

(56) References Cited

U.S. PATENT DOCUMENTS

| | | | |
|---|---|---|---|
| 2015/0037573 A1* | 2/2015 | Amano | C09J 7/29 |
| | | | 428/354 |
| 2015/0147556 A1 | 5/2015 | Sasaki et al. | |
| 2019/0090810 A1 | 3/2019 | Nagai et al. | |
| 2020/0093439 A1 | 3/2020 | Yoshioka | |

FOREIGN PATENT DOCUMENTS

| | | |
|---|---|---|
| EP | 3683275 A1 | 7/2020 |
| JP | 61-137539 A | 6/1986 |
| JP | H5-207983 A | 8/1993 |
| JP | 2003-342541 A | 12/2003 |
| JP | 2004-83425 A | 3/2004 |
| JP | 2012-10978 A | 1/2012 |
| JP | 2016-166436 A | 9/2016 |
| JP | 2018-103057 A | 7/2018 |
| JP | 2019-34440 A | 3/2019 |
| WO | 2017/183463 A1 | 10/2017 |
| WO | 2018/198456 A1 | 11/2018 |

OTHER PUBLICATIONS

Office Action issued on Jan. 12, 2024 for corresponding Chinese Patent Application No. 202080018974.6, along with partial English translation (12 pages).

Office Action issued on Feb. 27, 2024 for corresponding Japanese Patent Application No. 2019-42985, along with an English translation (16 pages).

International Search Report issued for corresponding International Patent Application No. PCT/JP2020/008643 on Apr. 21, 2020, along with an English translation.

Written Opinion issued for corresponding International Patent Application No. PCT/JP2020/008643 on Apr. 21, 2020.

Office Action issued on Oct. 11, 2022 for corresponding Japanese Patent Application No. 2019-042985, along with an English translation (5 pages).

Extended European Search Report issued on Mar. 23, 2022, for corresponding European Patent Application No. 20769578.4.

Chengxin Hu et al., "Stable, Strain-Sensitive Conductive Hydrogel with Antifreezing Capability, Remoldability, and Reusability", Applied Materials & Interfaces, Nov. 28, 2018, vol. 10, No. 50, pp. 44000-44010.

Office Action issued on Jul. 12, 2022 for corresponding Japanese Patent Application No. 2019-042985, along with an English machine translation (6 pages).

Office Action issued on Aug. 24, 2024 for corresponding Chinese Patent Application No. 202080018974.6 along with an English translation (10 pages).

Office Action issued on Dec. 19, 2024 for corresponding Chinese Patent Application No. 202080018974.6, along with an English machine translation (14 pages).

Office Action dated Apr. 2, 2025 for corresponding Chinese Patent Application No. 202080018974.6, along with an English translation (12 pages).

* cited by examiner

ELECTRODE AND BIOSENSOR

CROSS REFERENCE TO RELATED APPLICATION

This application is a National Stage of International Application No. PCT/JP2020/008643, filed on Mar. 2, 2020, which designates the United States and was published in Japan, and which is based upon and claims priority to Japanese Patent Application No. 2019-042985, filed on Mar. 8, 2019 in the Japan Patent Office. All of the aforementioned applications are hereby incorporated by reference in their entireties.

TECHNICAL FIELD

The present invention relates to an electrode and a biosensor.

BACKGROUND ART

In medical institutions such as hospitals and clinics, nursing facilities, and homes, biosensors are used for measuring biological information, for example, electrocardiograms, pulse waves, electroencephalograms, myoelectricity, or the like. A biosensor includes a bioelectrode that contacts a living body to obtain biological information of a test subject. When measuring biological information, a biosensor is affixed to a skin of a test subject to cause the bioelectrode to contact the skin of the test subject. The biological information is measured by obtaining electrical signals related to biological information through the bioelectrode.

As such a biosensor, a biocompatible polymer substrate that includes, for example, a polymer layer having an electrode on one surface, in which as the polymer layer, a layer constituted with dimethylvinyl-terminated dimethylsiloxane (DSDT) polymerized with tetramethyltetravinylcyclotetrasiloxane (TTC) by a predetermined ratio is used, is disclosed (see, e.g., Patent Document 1). In the biocompatible polymer substrate, the polymer layer is affixed to a skin of a person to cause the electrodes to detect a cardiac voltage signal from the skin of the person, and a module for data obtainment receives and records cardiac voltage signals.

RELATED ART DOCUMENTS

Patent Document

Patent Document 1: Japanese Laid-Open Patent Application No. 2012-10978

SUMMARY OF THE INVENTION

Problem to be Solved by the Invention

However, the biocompatible polymer substrate of Patent Document 1 is used by having the polymer layer affixed to the skin of the test subject; therefore, in some cases, the biocompatible polymer substrate is folded in the thickness direction, or depending on motion of the skin of the test subject, the biosensor may be pulled in a direction along the surface. Therefore, in the conventional biocompatible polymer substrate, there is a likelihood that the electrode is peeled off from a living body or the polymer layer. Also, due to the electrode being peeled off from the living body or the polymer layer, there is a likelihood that the electrical conductivity is not obtained stably.

One aspect of the present invention has an object to provide an electrode that is excellent in elasticity, and simultaneously, can maintain electrical conductivity.

Means for Solving the Problem

In one aspect according to the present invention, an electrode contains a conductive polymer; a binder resin; and a plasticizing agent, wherein the electrode has a plate shape having a pair of principal surfaces parallel to each other, and wherein a ratio of a content of the plasticizing agent to a content of the conductive polymer being 0.5 to 500.0 in a surface part of the electrode located at less than or equal to 1 μm from a surface of the electrode.

Advantageous Effect of the Present Invention

In one aspect according to the present invention, an electrode is excellent in elasticity, and simultaneously, can maintain electrical conductivity.

EMBODIMENTS FOR CARRYING OUT THE INVENTION

Figure 1:
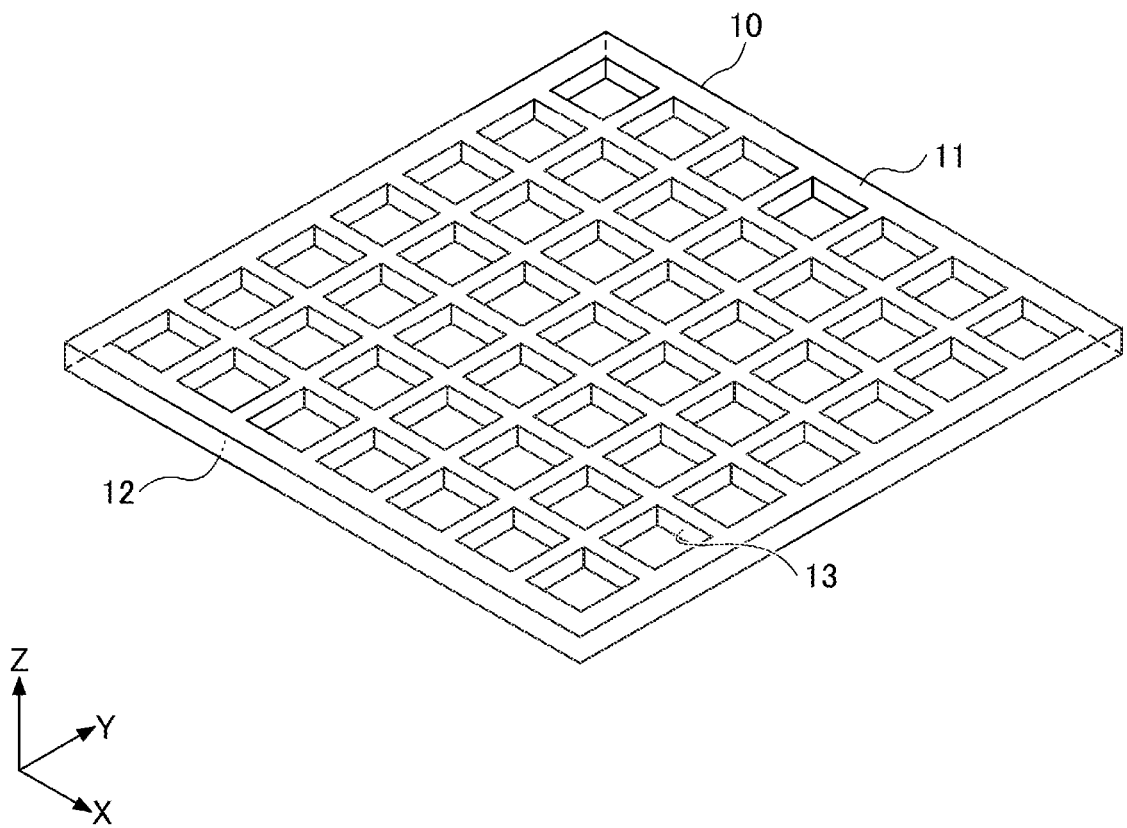
FIG. 1 is a perspective view of an electrode according to an embodiment.

In the following, embodiments according to the present invention will be described in detail. Note that in order to make the description easier to understand, the same elements throughout the drawings are assigned the same reference codes, and duplicate descriptions are omitted. Also, the scale of a member in the drawings may differ from an actual scale. In the present description, a three-dimensional orthogonal coordinate system having triaxial directions (X axis direction, Y axis direction, and Z axis direction) is used, and it is assumed that coordinates in a principal surface of an electrode are taken in the X axis direction and in the Y axis direction, and the height direction (thickness direction) corresponds to the Z axis direction. A direction from the bottom to the top of an electrode is referred to as the +Z axis direction and the opposite direction is referred to as the −Z axis direction. In the following description, for the sake of convenience of description, the +Z axis direction side will be referred to as the upper side or the top, and the −Z axis direction side will be referred to as the lower side or the bottom; however, these do not represent a universal vertical relationship. In the present specification, a tilde "~" indicating a numerical range is meant to include a lower limit and an upper limit that are given as numerical values before and after the tilde, unless otherwise noted.

<Electrode>

An electrode will be described according to an embodiment. FIG. 1 is a perspective view of an electrode according to an embodiment. As illustrated in FIG. 1, an electrode 10 is a plate-shaped (sheet-like) member having a pair of principal surfaces 11 and 12 parallel to each other, and has multiple holes 13 penetrating through the electrode 10 in the thickness direction (the Z axis direction), formed in a lattice pattern.

The principal surfaces 11 and 12 are flat surfaces. The principal surface 11 is a principal surface on one side (in the +Z axis direction) of the electrode 10, and serves as the top surface of the electrode 10. The principal surface 12 is a principal surface positioned in the direction opposite to the principal surface 11 (in the −Z axis direction), and serves as the bottom surface of the electrode 10. The principal surfaces 11 and 12 are formed to have a rectangular shape in plan view. Note that in the present embodiment, a rectangular shape means a rectangle, a square, or a rectangle or square having its corners chamfered.

The size of the electrode 10 in plan view can be designed appropriately. The thickness of the electrode 10 in plan view can be designed appropriately, and is favorably within a range of 0.1 µm to 100 µm. As long as the thickness of the electrode 10 is within a range 0.1 µm to 100 µm, the electrode 10 can have sufficient strength and.

The multiple holes 13 are arranged in a square lattice pattern on the principal surface 11, and are arrayed in the principal surface 11 with approximately equal intervals and in parallel with two crossing axial directions (the X axis direction and the Y axis direction). The holes 13 are all formed to have substantially the same size and shape. Note that the multiple holes 13 may not be equally spaced.

Each of the holes 13 is formed to have a rectangular shape in plan view. The size of the hole 13 can be designed appropriately depending on the size of the principal surface 11 and the like, and the length of each side is favorably 100 nm to 10 mm. Note that the shape of the hole 13 may be oblong. In the case where the shape of the hole 13 is oblong, it is favorable that the long side has a dimension of a numerical value as described above.

Although depending on the shape and size of the holes 13, the distance between the holes 13 is favorably 100 nm to 10 mm. Note that the distance between the holes 13 means a shortest distance between adjacent holes 13. The hole 13 is formed to have a rectangular shape in plan view; therefore, the distance between the holes 13 means the distance between the closest sides of the adjacent holes 13.

The electrode 10 can be formed using a conductive composition containing a conductive polymer, a binder resin, and a plasticizing agent.

As the conductive polymer, for example, polythiophene, polyacetylene, polypyrrole, polyaniline, polyphenylene vinylene, or the like can be used. Any of these may be used alone, or two or more may be used in combination. Among these, it is favorable to use a polythiophene compound. From the viewpoints of having a lower contact impedance with a living body and high electrical conductivity, it is more favorable to use PEDOT/PSS doped with polystyrenesulfonic acid (poly4-styrenesulfonate; PSS) in poly3,4-ethylenedioxythiophene (PEDOT).

The content of the conductive polymer is, with respect to 100 parts by mass of the conductive composition, favorably 0.20 to 20 parts by mass, more favorably 2.5 to 15 parts by mass, and even more favorably 3.0 to 12 parts by mass. As long as the content is, with respect to the conductive composition, within a range of 0.20 parts by mass to parts by mass, excellent electrical conductivity, toughness, and flexibility can be imparted to the conductive composition.

The conductive polymer may be used as an aqueous solution dissolved in a solvent. In this case, as the solvent, an organic solvent or an aqueous solvent can be used. As the organic solvent, for example, ketones such as acetone, methyl ethyl ketone (MEK), or the like; ester such as ethyl acetate; ethers such as propylene glycol monomethyl ether or the like; amides such as N, N-dimethylformamide, or the like, may be enumerated. As the aqueous solvent, for example, water; alcohol such as methanol, ethanol, propanol, isopropanol, or the like, may be enumerated. Among these, it is favorable to use an aqueous solvent.

As the binder resin, a water-soluble polymer, a water-insoluble polymer, or the like can be used. As the binder resin, it is favorable to use a water-soluble polymer from the viewpoint of compatibility with other components contained in the conductive composition. Note that the water-soluble polymer includes a hydrophilic polymer that is hydrophilic though not completely soluble in water.

As the water-soluble polymer, a hydroxyl group-containing polymer or the like can be used. As the hydroxyl group-containing polymer, sugars such as agarose or the like, polyvinyl alcohol (PVA), modified polyvinyl alcohol, a copolymer of acrylic acid and sodium acrylate, or the like can be used. Any of these may be used alone, or two or more may be used in combination. Among these, polyvinyl alcohol or modified polyvinyl alcohol is favorable, and modified polyvinyl alcohol is more favorable.

As the modified polyvinyl alcohol, acetoacetyl group-containing polyvinyl alcohol, diacetone acrylamide modified polyvinyl alcohol, or the like may be enumerated. Note that as the diacetone acrylamide modified polyvinyl alcohol, for example, a diacetone acrylamide modified polyvinyl alcohol-based resin (DA modified PVA-based resin) described in Japanese Laid-Open Patent Application No. 2016-166436 can be used.

The content of the binder resin is, with respect to 100 parts by mass of the conductive composition, favorably 5 to 140 parts by mass, more favorably 10 to 100 parts by mass, and even more favorably 20 to 70 parts by mass. As long as the content is within a range of 5 parts by mass to 140 parts by mass with respect to the conductive composition, excellent electrical conductivity, toughness, and flexibility can be imparted to the conductive composition.

The binder resin may be used as an aqueous solution dissolved in a solvent. As the solvent, a similar solvent can be used as in the case of the conductive polymer described above.

The plasticizing agent has function of giving toughness and flexibility to the conductive composition, and improves the tensile elongation and the flexibility of the conductive composition.

Note that the toughness is a property that makes excellent strength and elongation compatible with each other. The toughness does not include a property in which either one of the strength or elongation is remarkably excellent whereas the other is remarkably inferior, but includes a property in which both are balanced.

The flexibility is a property in that after having bent the electrode 10 obtained as a cured material of the conductive composition, occurrence of damage such as fracture in the bent part can be suppressed.

As the plasticizing agent, glycerin, ethylene glycol, propylene glycol, sorbitol, a polyol compound of these polymers or the like, N-methylpyrrolidone (NMP), an aprotonic compound such as dimethyl formaldehyde (DMF), N—N'-dimethylacetamide (DMAC), dimethyl sulfoxide (DMSO), or the like may be enumerated. Any of these may be used alone, or two or more may be used in combination. Among these, glycerin is favorable from the viewpoint of compatibility with the other components.

The content of the plasticizing agent is, with respect to 100 parts by mass of the conductive composition, favorably 0.2 parts by mass to 150 parts by mass, more favorably 1.0 parts by mass to 90 parts by mass, and even more favorably 10 parts by mass to 70 parts by mass. As long as the content is, with respect to 100 parts by mass of the conductive composition, within a range of 0.2 parts by mass to 150 parts by mass, excellent toughness and flexibility can be imparted to the conductive composition.

It is favorable that the conductive composition further includes a crosslinking agent. Like a plasticizing agent, a crosslinking agent has a function of giving toughness and flexibility to the conductive composition.

The crosslinking agent crosslinks the binder resin. By having the crosslinking agent contained in the binder resin, the toughness of the conductive composition can be improved. It is favorable that the crosslinking agent has reactivity with a hydroxyl group. If the crosslinking agent has reactivity with a hydroxyl group, in the case where the binder resin is a hydroxyl group-containing polymer, the crosslinking agent can react with hydroxyl groups of a hydroxyl group-containing polymer.

As the crosslinking agent, a zirconium compound such as zirconium salt; a titanium compound such as titanium salt; a borate such as boric acid; an isocyanate compound such as blocked isocyanate; an aldehyde compound such as dialdehyde such as glyoxal; an alkoxyl group-containing compound, a methylol group-containing compound, or the like may be enumerated. Any of these may be used alone, or two or more may be used in combination. Among these, a zirconium compound, isocyanate compound, or aldehyde compound is favorable from the viewpoint of the reactivity and the safety.

The content of the crosslinking agent is, with respect to 100 parts by mass of the conductive composition, favorably 0.2 to 80 parts by mass, more favorably 1 to 40 parts by mass, and even more favorably 3.0 to 20 parts by mass. As long as the content is, with respect to 100 parts by mass of the conductive composition, within a range of 0.2 parts by mass to 80 parts by mass, excellent toughness and flexibility can be imparted to the conductive composition.

The crosslinking agent may be used as an aqueous solution dissolved in a solvent. As the solvent, a similar solvent can be used as in the case of the conductive polymer described above.

The conductive composition contains at least one of the crosslinking agent and the plasticizing agent; therefore, the electrode 10 can be improved in terms of the toughness and the flexibility.

In the case where the plasticizing agent is contained in the conductive composition, but the crosslinking agent is not contained, the electrode can be improved in terms of the tensile elongation. Also, the flexibility of the electrode can be improved.

It is favorable that both the crosslinking agent and the plasticizing agent are contained in the conductive composition. By having both the crosslinking agent and the plasticizing agent contained in the conductive composition, more outstanding toughness can be imparted to the electrode 10.

In addition to the above components, the conductive composition may optionally contain a variety of publicly known additives such as a surfactant, a softening agent, a stabilizer, a leveling agent, an antioxidant, an anti-hydrolysis agent, a swelling agent, a thickener, a colorant, a bulking agent, and the like, by appropriate ratios, as necessary. As the surfactant, a silicone-based surfactant and the like may be enumerated.

The conductive composition is prepared by mixing the components described above by the ratios described above.

The conductive composition may optionally contain a solvent by an appropriate ratio, as necessary. In this way, an aqueous solution of the conductive composition (the aqueous solution of the conductive composition) is prepared.

As the solvent, an organic solvent or an aqueous solvent can be used. As the organic solvent, for example, ketones such as acetone, methyl ethyl ketone (MEK), or the like; ester such as ethyl acetate; ethers such as propylene glycol monomethyl ether or the like; amides such as N, N-dimethylformamide, or the like, may be enumerated. As the aqueous solvent, for example, water; alcohol such as methanol, ethanol, propanol, isopropanol, or the like, may be enumerated. Among these, it is favorable to use an aqueous solvent.

Figure 2:
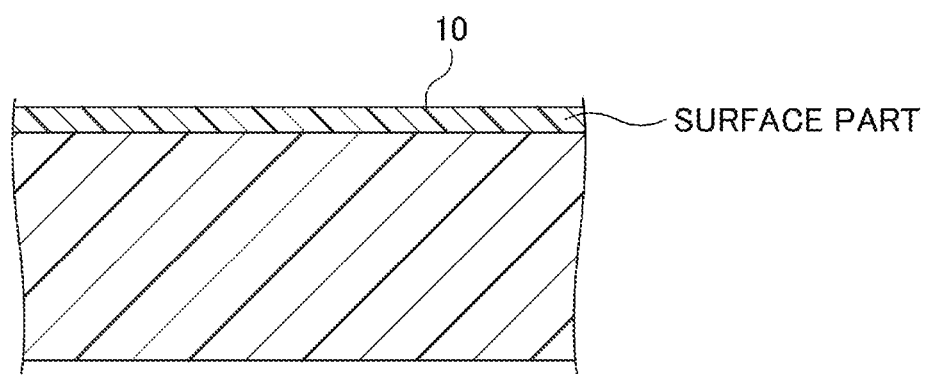
FIG. 2 is a partially enlarged cross sectional view of a surface of an electrode.

In the present embodiment, as illustrated in FIG. 2, in the surface part located at less than or equal to 1 μm in depth from the surface of the electrode 10 (the principal surfaces 11 and 12, and the edge surfaces), the ratio (M2/M1) of the content M2 of the plasticizing agent to the content M1 of the conductive polymer is 0.5 to 500.0, favorably 1.0 to 450.0, more favorably 3.5 to 400.0, and further more favorably 5.0 to 350.0. If M2/M1 in the surface part is less than 0.5, the ratio of the conductive polymer in the surface part increases, and the content of the plasticizing agent is concomitantly reduced. Consequently, the plasticizing agent does not function effectively, which thereby increases the modulus of elongation of the electrode 10. Therefore, the electrode 10 becomes hard and less stretchable and contractible. On the other hand, if M2/M1 in the surface part exceeds 500.0, the ratio of the plasticizing agent in the surface part increases, and the content of the conductive polymer is concomitantly reduced. Consequently, the electrical conductivity of the electrode 10 decreases. Also, the handleability of the electrode 10 tends to be reduced. If M2/M1 in the surface part is greater than or equal to 3.5, the surface part becomes more stretchable and contractible; therefore, occurrences of cracks can be reduced. If M2/M1 in the surface part is greater than or equal to 5.0, the amount of plasticizing agent that is deposited in the surface part can be reduced, and the electrical conductivity of the surface part can be stably maintained.

Note that in the present embodiment, in the surface part, the content M1 of the conductive polymer and the content M2 of the plasticizing agent can be measured by using publicly known measurement methods, and for example, can be measured by the infrared absorption spectrum, the Raman shift, or the like at any measurement point on the surface of the electrode 10 (the principal surfaces 11 and 12, and the edge surfaces), to calculate the ratios. It is favorable to execute the measurement at multiple points to improve the measurement precision.

The infrared absorption spectrum can be measured by the Fourier transform infrared spectrophotometer (FT-IR). By having the surface of the electrode 10 (the principal surfaces 11 and 12, and the edge surfaces) irradiated with infrared rays, fluctuations in the relative positions (molecular vibrations) between atoms (e.g., between O—H, between C—H, between C—O, between S—O, etc.) of components constituting the conductive polymer and the plasticizing agent can be examined.

The Raman shift can be measured by Raman spectroscopy. In Raman spectroscopy, by having the surface of the electrode 10 (the principal surfaces 11 and 12, and the edge surfaces) irradiated with light such as laser, scattered light generated by motion of molecules having polarizability is measured. In the surface of the electrode 10 (the principal surfaces 11 and 12, and the edge surfaces), peaks related to strain structures caused by bond angles between atoms of components of the conductive polymer and the plasticizing agent (e.g., H—C—H bond angle, C—O—C bond angle, O—C—C bond angle, C—S—C bond angle, S—C—C bond angle, etc.) are detected. In the case of using Raman spectroscopy, the conditions of Raman measurement can be set such that, for example, the laser wavelength being 532 nm (30 mW), the exposure time being 1 second, and the repeat count of accumulation being 20 times.

As for the measurement using FT-IR and the measurement by Raman spectroscopy, only one of these may be used, or both may be used. In the case of using both the measurement using FT-IR and the measurement by Raman spectroscopy, either one of the measurements may precede the other, or both may be measured simultaneously.

<Production Method of Electrode>

Figure 3:
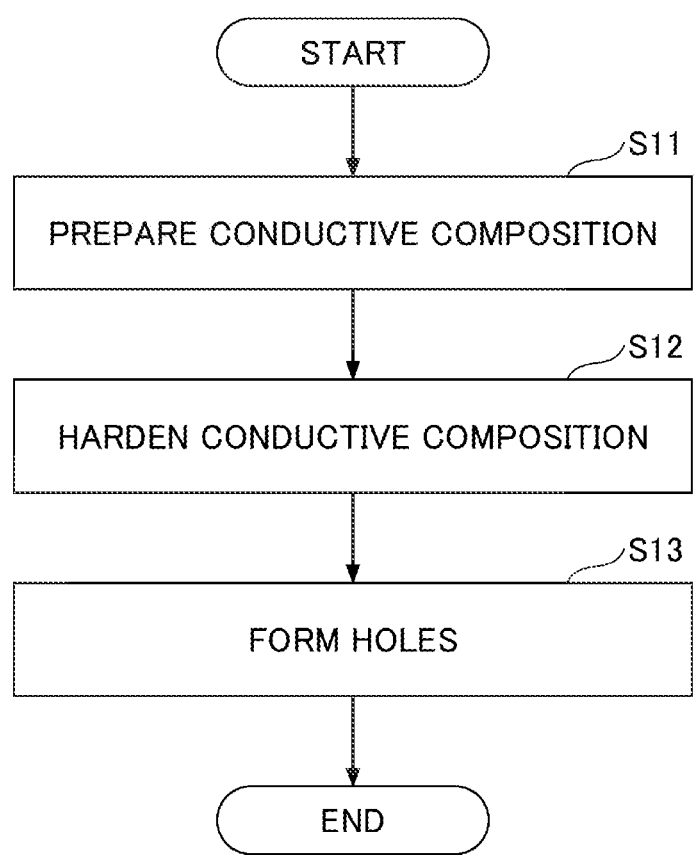
FIG. 3 is a flow chart illustrating a method of producing an electrode.

A production method of the electrode 10 will be described. FIG. 3 is a flow chart illustrating a method of producing the electrode 10. As illustrated in FIG. 3, the method of producing the electrode 10 includes a step of preparation of an aqueous solution of a conductive composition (Step S11); a step of curing the conductive composition (Step S12); and a step of forming holes in the cured material of the conductive composition (Step S13).

At the step of preparation (Step S11), a conductive polymer, a binder resin, and a plasticizing agent are mixed to prepare a conductive composition including the conductive polymer, the binder resin, and the plasticizing agent. In the present embodiment, in consideration of the content of the plasticizing agent in the surface part of the cured material of the conductive composition, the content of the plasticizing agent may be adjusted to an optimal amount as appropriate.

The conductive composition may further include a crosslinking agent.

The conductive composition can optionally contain a solvent by an appropriate ratio as necessary, to be treated as an aqueous solution of the conductive composition (the aqueous solution of the conductive composition).

At the step of curing the conductive composition (Step S12), after applying the conductive composition onto a surface of a peeling substrate, the peeling substrate onto which the conductive composition has been applied is heated by a dryer or the like. The heating removes the solvent in the conductive composition, and a crosslinking reaction of the binder resin is advanced by the crosslinking agent contained in the conductive composition, to cure the binder resin. In this way, a cured material of the conductive composition is obtained.

As the peeling substrate, a release liner, a core material, or the like can be used. As the release liner, a resin film such as a polyethylene terephthalate (PET) film, polyethylene (PE) film, polypropylene (PP) film, polyamide (PA) film, polyimide (PI) film, fluororesin film, or the like can be used. As the core material, a resin film such as a PET film or PI film; a ceramic sheet; a metal film such as aluminum foil; a resin substrate reinforced with fiberglass or plastic nonwoven fiber; a silicone substrate, a glass substrate, or the like can be used.

As the method of applying the conductive composition onto the peeling substrate, a method of roll coating, screen coating, gravure coating, spin coating, reverse coating, bar coating, blade coating, air knife coating, dipping, dispensing, or the like; a method of dripping a small amount of the conductive composition onto the substrate, that is then stretched with a doctor blade; or the like can be used. By these application methods, the conductive composition is uniformly applied onto the peeling substrate.

As the method of heating the conductive composition, a publicly known dryer such as a drying oven, a vacuum oven, an air circulation oven, a hot-air dryer, a far-infrared dryer, a microwave decompression dryer, a high-frequency dryer, or the like can be used.

As the heating condition, any condition can be adopted as long as the crosslinking agent contained in the conductive composition can react.

The heating temperature of the conductive composition is set to a temperature at which the reaction of crosslinking agent contained in the conductive composition can be advanced. The heating temperature is favorably 100° C. to 200° C., and more favorably 110° C. to 150° C. As long as the heating temperature is within a range of 100° C. to 200° C., the reaction of the crosslinking agent can be advanced readily, and curing of the binder resin can be advanced.

The heating time of the conductive composition is favorably 0.5 minutes to 300 minutes, and more favorably 5 minutes to 120 minutes. As long as the heating time is within a range of 0.5 to 300 minutes, the binder resin can be sufficiently cured.

In the present embodiment, during the curing process of the conductive composition, the content of the plasticizing agent in the surface part of the cured material of the conductive composition may be adjusted by, for example, a method of volatilizing a component that is bleeding out due to the plasticizing agent or the like on the surface of the cured material of the conductive composition; a method of cleaning the surface of the cured material of the conductive composition with alcohol or the like.

The obtained cured material is removed from the dryer while being placed on the peeling substrate.

At the step of forming holes (Step S13), the cured material is pressed by using a press machine or the like, to form multiple holes having a predetermined shape in the cured material. By this step, as illustrated in FIG. 1, a mesh-like electrode 10 is obtained in which holes 13 whose size and shape are substantially uniform, are formed to be arrayed in a square lattice pattern in the principal surface 11.

In this way, the electrode 10 is a sheet-like electrode containing a conductive polymer, a binder resin, and a plasticizing agent, and in the surface part of the electrode 10, the ratio (M2/M1) of the content M2 of the plasticizing agent to the content M1 of the conductive polymer is set to 0.5 to 15.0. The plasticizing agent improves the tensile elongation and the flexibility of the conductive composition, and hence, can increase the elasticity; however, there is a likelihood that the ratio of the conductive polymer in the conductive composition is reduced relatively, and hence, the electrical conductivity of the conductive composition is reduced. In particular, in the surface part of the electrode 10 that comes into contact with a contacted part, the ratios of the conductive polymer and the plasticizing agent tend to significantly affect the characteristics of the electrode 10. In the present embodiment, by setting M2/M1 in the surface part of the electrode 10 to 0.5 to 500.0, in the surface part, the respective functions of the conductive polymer and the plasticizing agent can be sufficiently exhibited without being hindered. In this way, the electrode can have the surface part sufficiently exhibit the elasticity, and simultaneously, hold the electrical conductivity. Therefore, the electrode can have an excellent elasticity, and simultaneously, can maintain the electrical conductivity, with respect to the contacted part on which the electrode 10 is placed.

The elasticity of the surface part of the electrode 10 with respect to the contacted part can be evaluated, for example, from the modulus of elongation of the electrode 10. The modulus of elongation of the electrode 10 can be measured by a method compliant with JIS K7161:2014 or the like. The modulus of elongation of the electrode 10 is, for example, at room temperature (23° C.), favorably less than or equal to 0.1 GPa, more favorably less than or equal to 0.080 GPa, and even more favorably less than or equal to 0.060 GPa. If the modulus of elongation of the electrode 10 becomes too high, the electrode 10 becomes hard and difficult to be stretched and contracted. In contrast, if the modulus of elongation of the electrode 10 becomes too low, although the electrode 10 becomes easier to be stretched and contracted, a reduction in the electrical conductivity of the electrode 10 is introduced. Therefore, it would be sufficient that the modulus of elongation of the electrode 10 is, for example, greater than or equal to 0.001 GPa. Therefore, if the modulus of elongation of the electrode 10 at room temperature (23° C.) is less than or equal to 0.1 GPa, the electrode 10 can alleviate stress generated by deformation of the contacted part on the surface part, and hence, can exhibit an excellent elasticity with respect to the contacted part.

In the case of determining the modulus of elongation of the electrode 10 according to JIS K7161:2014, a tensile test is conducted under conditions of a temperature being room temperature (23° C.) and a tensile speed of 100 mm/min, to obtain a stress-strain curve. Based on the obtained stress-strain curve, by determining slopes of the curve at two points at which the strains are 0.05% and 0.25%, respectively, the modulus of elongation at room temperature (e.g., 23° C.±2° C.) can be calculated. Specifically, denoting the value of strain of the electrode 10 (in units of %) being 0.05% by $\varepsilon 1$, the value of strain being 0.25% by $\varepsilon 2$, and the stress corresponding to $\varepsilon 1$ and $\varepsilon 2$ (in units of MPa) by $\sigma 1$ and $\sigma 2$, respectively, as expressed in the following formula (1), the modulus of elongation E (in units of MPa) at room temperature (e.g., 23° C.±2° C.) can be obtained by dividing the difference in stress ($\sigma 2-\sigma 1$) by the difference in strain ($\varepsilon 22-\varepsilon 1$).

$$E=(\sigma 2-\sigma 1)/(\varepsilon 2-\varepsilon 1) \quad (1)$$

Also, thanks to the surface part exhibiting an excellent elasticity with respect to the contacted part on which the electrode 10 is placed, the electrode 10 can exhibit an excellent handleability, and can be easy to handle.

The electrode 10 can have multiple holes 13 penetrating through the principal surface 11 in the thickness direction. In this way, when the adhesive layer is formed on the principal surface 11 side of the electrode 10, the adhesive layer can come into contact with the contacted part through the holes 13. Therefore, the electrode 10 can connect the adhesive layer to the contacted part.

The electrode 10 can be configured to have the holes 13 arranged in a square lattice pattern on the principal surface 11. With this arrangement, when the adhesive layer is formed on the electrode 10, the adhesive layer can contact the contacted part substantially equally around the entire perimeter of the electrode 10 through the holes 13 in the electrode 10, and the contact area of the electrode 10 to the contacted part can be secured substantially evenly. Therefore, when the adhesive layer is formed on the principal surface 11 side, even if stretching or contraction occurs in any direction of the contacted part, the adhesive layer can stably maintain the adhesive strength to the contacted part, and the electrode 10 can stably maintain the electrical conduction with the contacted part.

The electrode 10 can use glycerin as the plasticizing agent. Glycerin is excellent in compatibility with the other components in the conductive composition, and hence, likely to improve the tensile elongation and the flexibility of the conductive composition, and to increase the handleability of the conductive composition. Also, by using glycerin as the plasticizing agent, in the case of using polyvinyl alcohol as the binder resin, the tensile elongation can be further improved.

As such, the electrode 10 has the characteristics described above, and hence, can be applied to the material of an electrode for a biosensor, an electrode for a battery, an electrode for a touch screen panel, an electrode for a solar battery, an electrode for electroluminescence, an electrode for a capacitor, an actuator elements, a thermoelectric transducer, and the like. Among these, the electrode 10 can be suitably used as the electrode of a patch-type biosensor attached to the skin or the like of a living body, that requires stable adhesive strength and electrical conductivity.

<Biosensor>

A biosensor to which the electrode 10 according to one embodiment is applied will be described. The electrode 10 is used as a probe of the biosensor. In the present embodiment, as an example, a case will be described in which a patch-type biosensor is affixed to a living body to measure biometric information. Note that the living body here includes a human body (a person) and animals such as cattle, horses, pigs, chickens, dogs, cats, and the like. The biosensor is affixed to part of the living body (e.g., skin, scalp, forehead, etc.). The biosensor can be suitably used for living bodies, in particular for human bodies.

Figure 4:
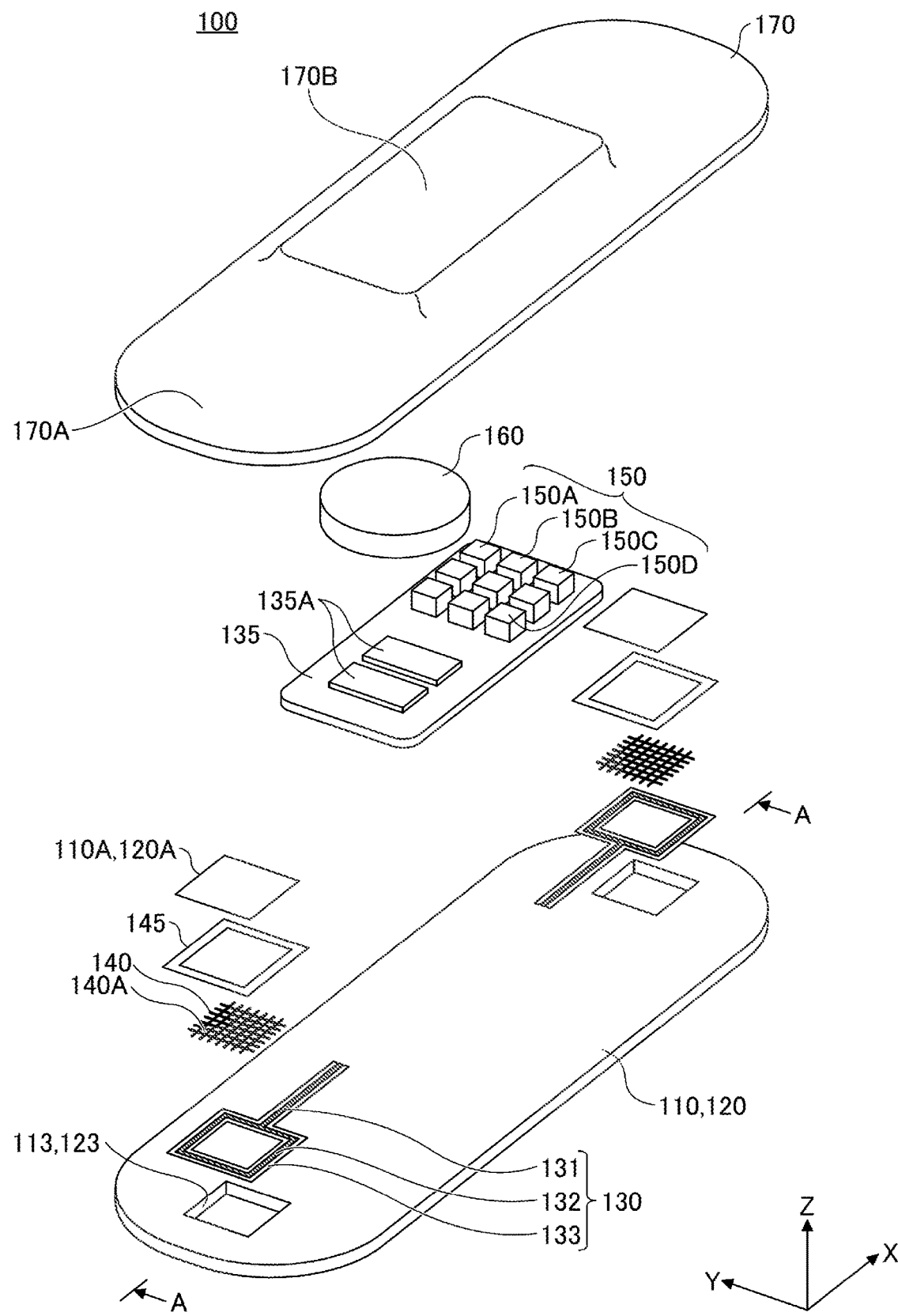
FIG. 4 is an exploded view illustrating a patch-type biosensor.
Figure 5:
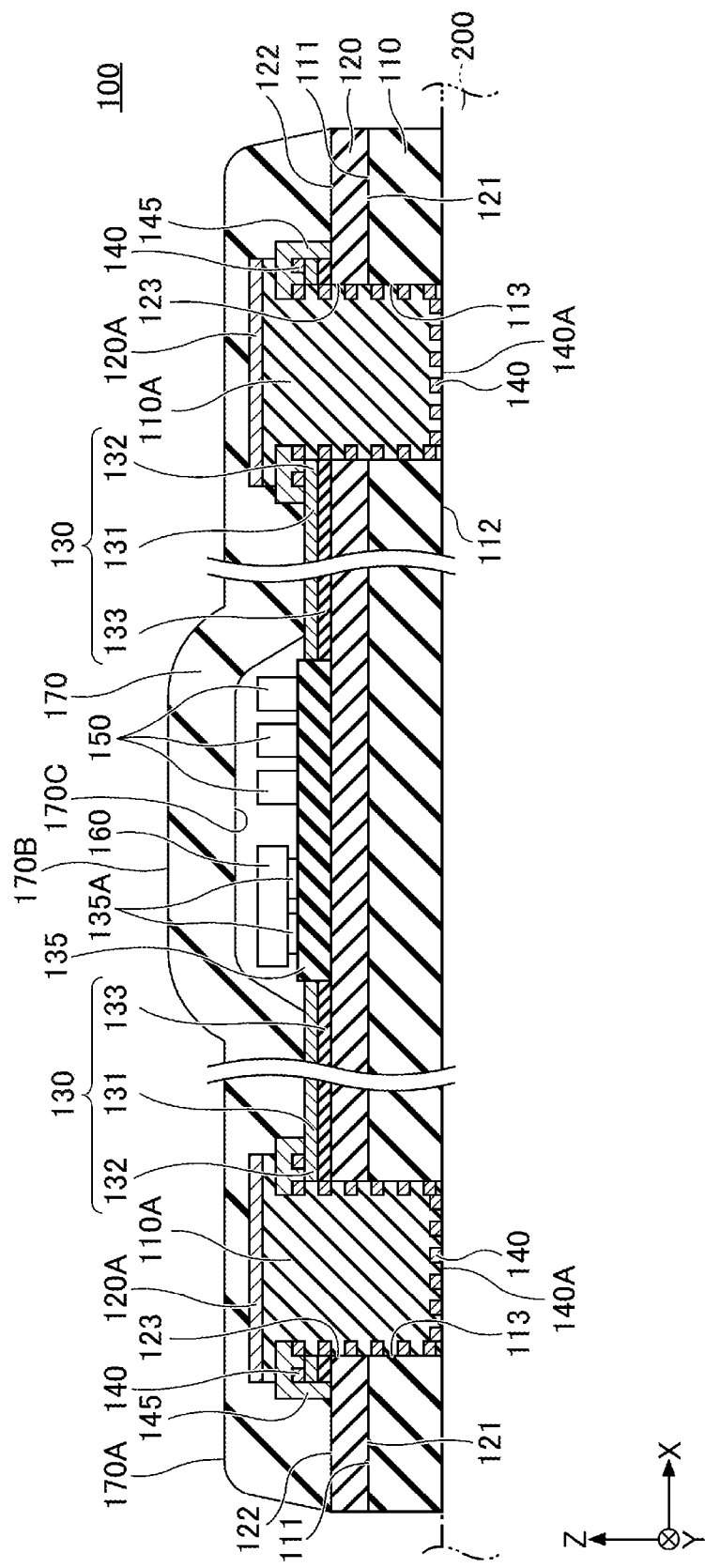
FIG. 5 is a diagram illustrating a cross section in a completed state corresponding to a cross section viewed in the direction of arrows A-A in FIG. 4.

FIG. 4 is an exploded view illustrating a patch-type biosensor according to an embodiment. FIG. 5 is a diagram illustrating a cross section in a completed state corresponding to a cross section viewed in the direction of arrows A-A in FIG. 4. As illustrated in FIGS. 4 and 5, a patch-type biosensor 100 according to an embodiment includes a pressure-sensitive adhesive layer 110, a base material layer 120, circuit parts 130, a substrate 135, probes 140, fixing tapes 145, an electronic device 150, a battery 160, and a cover 170, as major components. In the following, the respective members constituting the patch-type biosensor 100 will be described.

The patch-type biosensor 100 is a sheet-like member having a generally elliptic shape in plan view. The patch-type biosensor 100 is covered with the cover 170 on the top surface opposite to the bottom surface (a surface on the −Z direction side) that is to be affixed to a skin 200 of a living body. The bottom surface of the patch-type biosensor 100 is the affixing surface.

The circuit part 130 and the substrate 135 are mounted on the top surface of the base material layer 120. Also, the probe 140 is provided in a form of being embedded in the pressure-sensitive adhesive layer 110 so as to be exposed from a bottom surface 112 of the pressure-sensitive adhesive layer 110. The bottom surface 112 is the affixing surface of the patch-type biosensor 100.

The pressure-sensitive adhesive layer 110 is a flat plate-shaped adhesive layer. The pressure-sensitive adhesive layer 110 is oriented to have its longitudinal direction extend in the X axis direction and its short direction extend in the Y axis direction. The pressure-sensitive adhesive layer 110 is supported by the base material layer 120, and is affixed to a bottom surface 121 of the base material layer 120.

As illustrated in FIG. 5, the pressure-sensitive adhesive layer 110 has a top surface 111 and a bottom surface 112. The top surface 111 and the bottom surface 112 are flat surfaces. The pressure-sensitive adhesive layer 110 is a layer with which the patch-type biosensor 100 contacts the living body. The bottom surface 112 has pressure-sensitive adhesiveness, and hence, can be affixed to the skin 200 of the living body. The bottom surface 112 is the bottom surface of the patch-type biosensor 100, and can be affixed to a biological surface such as the skin 200.

The material of the pressure-sensitive adhesive layer 110 is not limited in particular as long as being a material having pressure-sensitive adhesiveness, and a material having biocompatibility or the like may be enumerated. As the material of the pressure-sensitive adhesive layer 110, an acryl-based pressure-sensitive adhesive, silicone-based pressure-sensitive adhesive, or the like may be enumerated. Favorably, an acryl-based pressure-sensitive adhesive may be recommended.

The acryl-based pressure-sensitive adhesive contains an acrylic polymer as the main component.

The acrylic polymer is a pressure-sensitive adhesive component. As the acrylic polymer, a polymer polymerized with a monomer component that contains (meth)acrylic ester such as isononyl acrylate, methoxyethyl acrylate, or the like as the main component, and contains a monomer copolymerizable with (meth)acrylic ester such as acrylic acid or the like as an optional component, can be used. The content of the main component among the monomer components is 70 mass % to 99 mass %, and the content of the optional component among the monomer components is 1 mass % to 30 mass %. As the acrylic polymer, for example, a (meth) acrylic ester-based polymer described in Japanese Laid-Open Patent Application No. 2003-342541, or the like can be used.

Favorably, the acryl-based pressure-sensitive adhesive further contains carboxylic acid ester.

The carboxylic acid ester contained in the acryl-based pressure-sensitive adhesive is a pressure-sensitive adhesiveness modifier that reduces the pressure-sensitive adhesiveness of the acrylic polymer, to modify the pressure-sensitive adhesiveness of the pressure-sensitive adhesive layer 110. The carboxylic acid ester is a carboxylic acid ester compatible with an acrylic polymer.

Specifically, the carboxylic acid ester is tri-fatty acid glyceryl, as an example.

The content of carboxylic acid ester is, with respect to 100 parts by mass of the acrylic polymer, favorably 30 parts by mass to 100 parts by mass, and more favorably 50 parts by mass to 70 parts by mass.

The acryl-based pressure-sensitive adhesive may contain a crosslinking agent as necessary. The crosslinking agent is a crosslinking component that crosslinks the acrylic polymer. As the crosslinking agent, a polyisocyanate compound, epoxy compound, melamine compound, peroxide compound, urea compound, metal alkoxide compound, metal chelate compound, metal salt compound, carbodiimide compound, oxazoline compound, aziridine compound, amine compound, or the like may be enumerated. Any of these crosslinking agents may be used alone, or two or more may be used in combination. As the crosslinking agent, favorably, a polyisocyanate compound (polyfunctional isocyanate compound) may be recommended.

The content of crosslinking agent is, with respect to 100 parts by mass of the acrylic polymer, for example, favorably 0.001 parts by mass to 10 parts by mass, and more favorably 0.01 parts by mass to 1 part by mass.

It is favorable that the pressure-sensitive adhesive layer 110 has an excellent biocompatibility. For example, when the pressure-sensitive adhesive layer 110 undergoes a keratin peeling test, the ratio of keratin-peeled area is favorably 0% to 50%, and more favorably 1% to 15%. As long as the ratio of keratin-peeled area is within a range of 0% to 50%, the load imposed on the skin 200 (see FIG. 5) can be suppressed even if the pressure-sensitive adhesive layer 110 is affixed to the skin 200 (see FIG. 5). Note that the keratin peeling test is measured by a method described in Japanese Laid-Open Patent Application No. 2004-83425.

The moisture permeability of the pressure-sensitive adhesive layer 110 is favorably greater than or equal to 300 $g/m^2$ day, more favorably greater than or equal to 600 $g/m^2$ day, and even more favorably greater than or equal to 1,000 $g/m^2$ day. As long as the moisture permeability of the pressure-sensitive adhesive layer 110 is greater than or equal to 300 $g/m^2$ day, the load imposed on the skin 200 (see FIG. 5) can be suppressed even if the pressure-sensitive adhesive layer 110 is affixed to the skin 200 (see FIG. 5) of the living body.

The pressure-sensitive adhesive layer 110 comes to have biocompatibility by satisfying at least one of the following requirements: the ratio of keratin-peeled area in the keratin peeling test is less than or equal to 50%; and the moisture permeability is greater than or equal to 300 $g/m^2$ day. It is more favorable that the material of the pressure-sensitive adhesive layer 110 satisfies both of the requirements described above. This enables the pressure-sensitive adhesive layer 110 to have a higher biocompatibility more stably.

The thickness between the top surface 111 and bottom surface 112 of the pressure-sensitive adhesive layer 110 is favorably 10 μm to 300 μm. If the thickness of the pressure-sensitive adhesive layer 110 is within a range of 10 μm to 95 μm, the patch-type biosensor 100 can be made thinner, especially in a region other than the electronic device 150 in the patch-type biosensor 100.

The base material layer 120 is a support layer that supports the pressure-sensitive adhesive layer 110, and the pressure-sensitive adhesive layer 110 is bonded to the bottom surface 121 of the base material layer 120. The circuit part 130 and the substrate 135 are arranged on the top surface of the base material layer 120.

The base material layer 120 is a flat plate-shaped (sheet-like) member made of an insulator. The shape of the base material layer 120 in plan view is the same as the shape of the pressure-sensitive adhesive layer 110 in plan view, and these are stacked at aligned positions in plan view.

The base material layer 120 has the bottom surface 121 and a top surface 122. The bottom surface 121 and the top surface 122 are flat surfaces. The bottom surface 121 contacts the top surface 111 of the pressure-sensitive adhesive layer 110 (by pressure-sensitive bonding). The base material layer 120 simply needs to be made of a flexible resin having moderate elasticity, flexibility, and toughness, and may be made of thermoplastic resin such as, for example, polyurethane-based resin, silicone-based resin, acryl-based resin, polystyrene-based resin, vinyl chloride-based resin, and polyester-based resin.

The thickness of the base material layer 120 is favorably within a range of 1 μm to 300 μm, more favorably within a range of 5 μm to 100 μm, and even more favorably within a range of 10 μm to 50 μm.

The circuit part 130 includes a wire 131, a frame 132, and a substrate 133. The patch-type biosensor 100 includes two instances of such a circuit part 130. The wire 131 and the frame 132 are provided on the top surface of the substrate 133, and formed integrally. The wire 131 connects the frame 132 to the electronic device 150 and the battery 160.

The wire 131 and the frame 132 can be made of copper, nickel, gold, an alloy of these, or the like. The thickness of the wire 131 and the frame 132 is favorably within a range of 0.1 μm to 100 μm, more favorably within a range of 1 μm to 50 μm, and even more favorably within a range of 5 μm to 30 μm.

Each of the two instances of the circuit part 130 is provided corresponding to two through holes 113 and 123 of the pressure-sensitive adhesive layer 110 and of the base material layer 120, respectively. The wire 131 is connected to the electronic device 150 and a terminal 135A for the battery 160 via wires of the substrate 135. The frame 132 is a rectangular loop-shaped conductive member larger than the opening of the through hole 123 of the base material layer 120.

The substrate 133 has a shape substantially the same as that of the wire 131 and the frame 132 in plan view. Part of the substrate 133 on which the frame 132 is provided has a rectangular loop shape larger than the opening of the through hole 123 of the base material layer 120. The frame 132 and the rectangular loop-shaped part of the substrate 133 on which the frame 132 is provided, are provided to surround the through hole 123 on the top surface of the base material layer 120. The substrate 133 simply needs to be made of an insulator material, and for example, a substrate or film made of polyimide or the like can be used. The base material layer 120 has tackiness; therefore, the substrate 133 is fixed to the top surface of the base material layer 120.

The substrate 135 is a substrate made of an insulator material, to have the electronic device 150 and the battery 160 mounted, and provided on the top surface 122 of the base material layer 120. The substrate 135 is fixed by the tackiness of the base material layer. As the substrate 135, a substrate or film made of polyimide or the like can be used, as an example. On the top surface of the substrate 135, wires and the terminal 135A for the battery 160 are provided. The wires of the substrate 135 are connected to the electronic device 150 and the terminal 135A, and to the wire 131 of the circuit part 130.

The probe 140 is an electrode that contacts the skin 200, to detect biological signals, when the pressure-sensitive adhesive layer 110 is affixed to the skin 200. The biological signal is, for example, an electrical signal representing an electrocardiographic waveform, electroencephalogram, pulse, or the like.

As the probe 140, the electrode 10 according to an embodiment is used; therefore, detailed description of the materials that form the probe 140 is omitted.

The probe 140 has a rectangular shape in plan view, and has holes 140A arranged in a matrix that is larger than the respective through holes 113 and 123 of the pressure-sensitive adhesive layer 110 and of the base material layer 120. At the ends (end parts of four sides) in the X direction and the Y direction of the probe 140, the ladder-like sides of the probe 140 may protrude.

The fixing tape 145 is, as an example, a copper tape, and has a rectangular loop shape in plan view. The fixing tape 145 has its bottom surface coated with an adhesive. The fixing tape 145 is provided on the frame 132 so as to surround the four sides of the probe 140 on the outside of the opening of the through holes 113 and 123 in plan view, to fix the probe 140 to the frame 132. The fixing tape 145 may be a tape of metal other than copper.

The probe 140 is fixed to the frame 132 by the fixing tape 145 that covers edge parts along the four sides, in a state of the edge parts along the four sides being arranged on the frame 132. The fixing tape 145 is adhered to the frame 132 through gaps such as the holes 140A in the probe 140.

In a state of the probe 140 having its edge parts along the four sides fixed on the frame 132 by the fixing tape 145 in this way, the pressure-sensitive adhesive layer 110A and the base material layer 120A are overlaid on the fixing tape 145 and the probe 140. When the pressure-sensitive adhesive layer 110A and the base material layer 120A are pressed downward, the probe 140 is pushed along the inner walls of the through holes 113 and 123, and the pressure-sensitive adhesive layer 110A is pushed into the interior of the holes 140A in the probe 140.

The probe 140 is pushed down to a position at which its center part becomes substantially flush with the bottom surface 112 of the pressure-sensitive adhesive layer 110, in a state of its edge parts along the four sides being fixed to the frame 132 by the fixing tape 145. Therefore, if having the probe 140 come in contact with the skin 200 of the living body (see FIG. 5), the pressure-sensitive adhesive layer 110A can be adhered to the skin 200, and the probe 140 can be firmly adhered to the skin 200.

It is favorable that the thickness of the probe 140 is thinner than the thickness of the pressure-sensitive adhesive layer 110. The thickness of the probe 140 is favorably within a range of 0.1 μm to 100 μm, and more favorably within a range of 1 μm to 50 μm.

Also, the surrounding part (rectangular loop-shaped part) surrounding the central part of the pressure-sensitive adhesive layer 110A in plan view is positioned above the fixing tape 145. In FIG. 5, although the top surface of the pressure-sensitive adhesive layer 110A is generally flat, the center part may be recessed downward compared to the surrounding part. The base material layer 120A is overlaid on the generally flat top surface of the pressure-sensitive adhesive layer 110A.

The pressure-sensitive adhesive layer 110A and the base material layer 120A as such may be made of the same materials as the pressure-sensitive adhesive layer 110 and the base material layer 120, respectively. Also, the pressure-sensitive adhesive layer 110A may be made of a material different from that of the pressure-sensitive adhesive layer 110. Also, the base material layer 120A may be made of a material different from that of the base material layer 120.

Note that in FIG. 5, although the thicknesses of the respective parts are exaggerated, in practice, the thicknesses of the pressure-sensitive adhesive layer 110 and 110A is within a range of 10 μm to 300 μm, and the thicknesses of the base material layer 120 and 120A is within a range of 1 μm to 300 μm. Also, the thicknesses of the wire 131 is within a range of 0.1 μm to 100 μm, the thicknesses of the substrate 133 is around several 100 μm, and the thicknesses of the fixing tape 145 is within a range of 10 μm to 300 μm.

Also, as illustrated in FIG. 5, in the case where the probe 140 directly contacts the frame 132, and the electrical connection is secured, the fixing tape 145 may be a tape made of resin or the like that does not have electrical conductivity.

Also, in FIG. 5, the fixing tape 145 covers the side surfaces of the frame 132 and the substrate 133 in addition to the probe 140, and reaches the top surface of the base material layer 120. However, the fixing tape 145 simply needs to have the probe 140 and the frame 132 joined, and hence, does not need to reach the top surface of the base material layer 120; does not need cover the side surfaces of the substrate 133; and does not need cover the side surfaces of the frame 132.

Also, the substrate 133 and the two substrates 135 may be one integrated substrate. In this case, the wires 131, the two frames 132, and the terminal 135A are provided on a surface of the one substrate, to have the electronic device 150 and the battery 160 mounted.

The electronic device 150 is formed on the top surface 122 of the base material layer 120, and electrically connected to the wires 131. The electronic device 150 has a rectangular shape in cross sectional view. The bottom surface (in the −Z direction) of the electronic device 150 is provided with terminals. As the material of the terminals of the electronic device 150, solder, conductive paste, or the like may be enumerated.

As illustrated in FIG. 4, the electronic device 150 includes, as an example, an application specific integrated circuit (ASIC) 150A, a micro processing unit (MPU) 150B, a memory 150C, and a wireless communication unit 150D; and is connected to the probes 140 via the circuit parts 130 and the battery 160.

The ASIC 150A includes an A/D (Analog to Digital) converter. The electronic device 150 is driven by electric power supplied from the battery 160, to obtain biological signals measured by the probes 140. The electronic device 150 executes processing such as filtering and digital conversion on the biological signals, and the MPU 150B calculates an arithmetic mean of values of the biological signals obtained multiple times, to store the mean in the memory 150C. The electronic device 150 can obtain biological signals continuously, as an example, for 24 hours or longer. In some cases, the electronic device 150 measures biological signals for a long period of time; therefore, various ideas are incorporated to reduce the electric power consumption.

The wireless communication unit 150D is a transceiver used when a test device of an evaluation test reads biological signals stored in the memory 150C during the evaluation test via the wireless communication, and executes communication, as an example, at 2.4 GHz. The evaluation test is a test, as an example, compliant with the standard of JIS 60601-2-47. The evaluation test is a test executed after completion of a biosensor, to verify operations of the biosensor to detect biological signals as a medical device. The evaluation test requires an attenuation factor of a biological signal extracted from the biosensor being less than 5% with respect to a biological signal input into the biosensor. This evaluation test is to be executed for all completed products.

As illustrated in FIG. 5, the battery 160 is provided on the top surface 122 of the base material layer 120. As the battery 160, a lead battery, a lithium ion secondary battery, or the like can be used. The battery 160 may be a button battery. The battery 160 is an example of a battery. The battery 160 has terminals provided on its bottom surface. The terminals of the battery 160 are connected to the probes 140 via the circuit parts 130, and the electronic device 150. The capacity of the battery 160 is set so that the electronic device 150 can measure biological signals, as an example, for 24 hours or longer.

The cover 170 covers the base material layer 120, the circuit parts 130, the substrate 135, the probes 140, the fixing tapes 145, the electronic device 150, and the battery 160. The cover 170 has a base part 170A and a protruding part 170B protruding in the +Z direction from the center of the base part 170A. The base part 170A is a part positioned at the periphery of the cover 170 in plan view, and is a part positioned lower than protruding part 170B. A recessed part 170C is provided below the protruding part 170B. In the cover 170, the bottom surface of the base part 170A is adhered to the top surface 122 of the base material layer 120. In the recessed part 170C, the substrate 135, the electronic device 150, and the battery 160 are housed. The cover 170 is bonded to the top surface 122 of the base material layer 120 in a state of having the electronic device 150, the battery 160, and the like housed in the recessed part 170C.

In addition to the role of serving as a cover for protecting the circuit parts 130, the electronic device 150, and the battery 160 on the base material layer 120, the cover 170 has a role of serving as a shock absorbing layer to protect the interior components from shocks applied to the patch-type biosensor 100 from the top surface side. As the cover 170, for example, silicone rubber, soft resin, urethane, or the like can be used.

Figure 6:
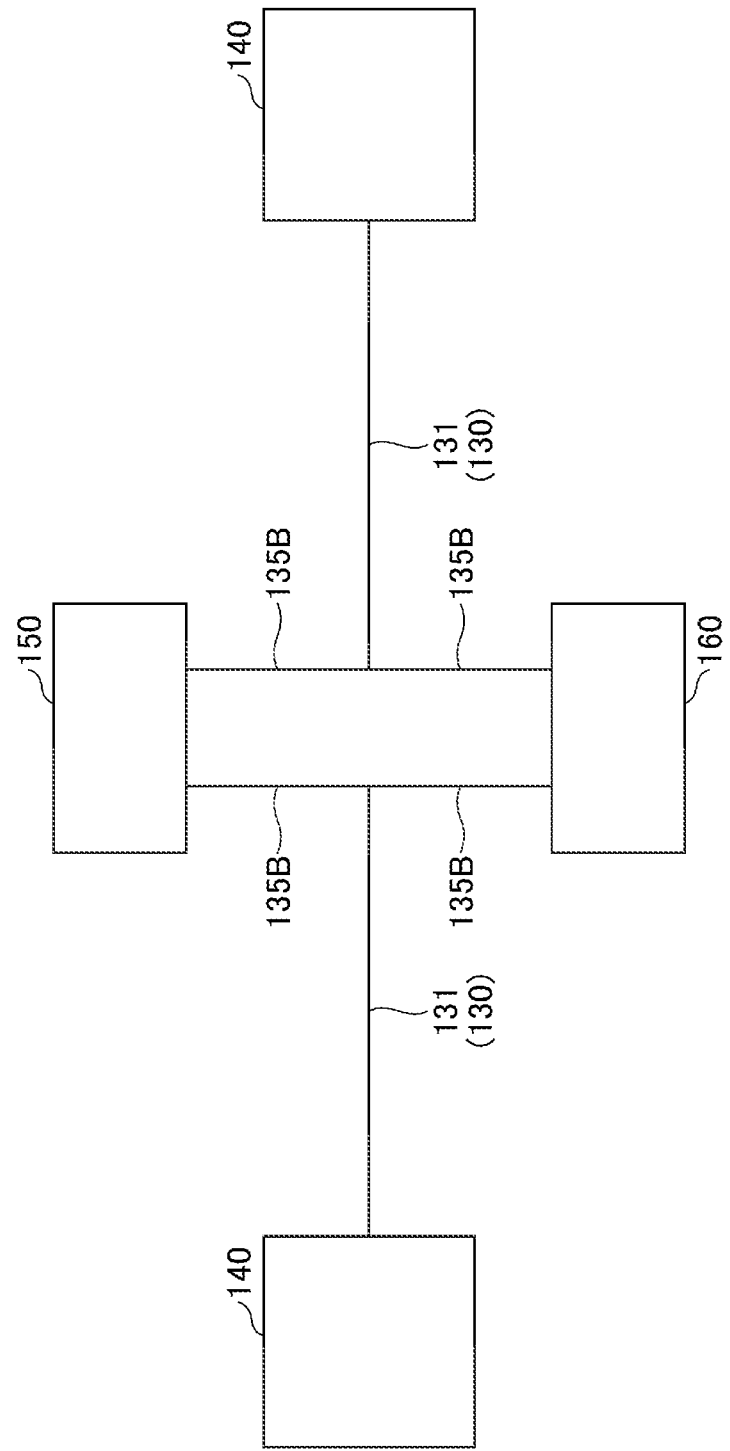
FIG. 6 is a diagram illustrating a circuit configuration of a patch-type biosensor.

FIG. 6 is a diagram illustrating a circuit configuration of the patch-type biosensor 100. Each of the probes 140 is connected to the electronic device 150 and the battery 160 via the wire 131 and the wire 135B of the substrate 135. The two probes 140 are connected in parallel to the electronic device 150 and the battery 160.

In this way, the patch-type biosensor 100 uses the electrode 10 according to one embodiment described above (see FIG. 1) as the probe 140, and the probe 140 has excellent elasticity in its surface part with respect to the contacted part, and simultaneously, holds the electrical conductivity. Even if the surface of the skin of a test subject moves in a state of the probe 140 being adhered to the pressure-sensitive adhesive layer 110, the probe 140 of the patch-type biosensor 100 can be easily stretched and contracted in accordance with the motion of the skin. Therefore, the patch-type biosensor 100 can easily maintain a state of the pressure-sensitive adhesive layer 110 being adhered to the skin through the holes 140A in the probe 140; therefore, the probe 140 can be prevented from peeling off from the skin. Also, the patch-type biosensor 100 can secure the electrical conductivity in the probe 140, and hence, can stably hold the electrical conductivity with the skin. Therefore, the patch-type biosensor 100 is resistant to be peeled off from the skin, and can maintain the electrical conductivity; therefore, even if the patch-type biosensor 100 is affixed to the skin, and used for a long period of time, the patch-type biosensor 100 can stably measure biometric information.

The patch-type biosensor 100 can have multiple holes 140a in the probe 140 that penetrate through the principal surface in the thickness direction. By having the pressure-sensitive adhesive layer 110 on the probe 140 come into contact with a contacted part through the holes 140A, the patch-type biosensor 100 can have the pressure-sensitive adhesive layer 110 stably connect to the skin through the holes 140A in the probe 140, and hence, can exhibit the adhesive strength to the skin of the pressure-sensitive adhesive layer 110.

The patch-type biosensor 100 can be configured to have the holes 140A in the probe 140 arranged in a square lattice pattern on the principal surface. In this way, This enables the pressure-sensitive adhesive layer 110 to contact the skin substantially equally around the entire perimeter of the probe 140 through the holes 140A, and the contact area of the probe 140 to the skin can be secured substantially evenly. Therefore, Therefore, even if the surface of the skin moves, and the skin contacting the probe 140 stretches or contracts in any direction, the patch-type biosensor 100 can have the pressure-sensitive adhesive layer 110 stably maintain a state of being affixed to the skin through the holes 140A of the probe 140.

After being used for measuring biometric information, the patch-type biosensor 100 can be recovered as necessary to remove the electronic device 150 and the battery 160, and by replacing these components, can be reused.

The patch-type biosensor 100 is a measurement device that senses electrical signals from a living body to measure biological information, and can be used as a patch-type electrocardiogram, patch-type electroencephalograph, patch-type blood pressure manometer, patch-type pulse meter, patch-type myometer, patch-type thermometer, patch-type accelerometer, or the like.

Among these applications, the patch-type biosensor 100 is favorably used as a patch-type electrocardiogram. In electrocardiography, by having the patch-type biosensor 100 obtain as biological information minute action potentials (electromotive forces) of the myocardium that occur with the heartbeat of a test subject, abnormal electrocardiograms such as arrhythmias and ischemic heart disease can be investigated. In electrocardiography, the patch-type biosensor 100 being affixed to the chest, both wrists, both ankles, or the like of a test subject can stably detect, as electrical signals, myocardial active potentials generated by the heartbeat of the test subject by the probes 140. Therefore, by using the electrical signals detected by the probes 140, the patch-type biosensor 100 can obtain electrocardiogram waveforms more precisely.

MODIFIED EXAMPLES

Note that in the present embodiment, the electrode 10 may not have the holes 13.

In the present embodiment, the holes 13 can be formed at optimal positions, in an optimal size, and the like depending on the number formed in the principal surface 11 of the electrode 10.

In the present embodiment, the arrangement of the holes 13 is not limited to be a square lattice pattern, and may be an oblique lattice pattern or a hexagonal (staggered) lattice pattern. Also, the multiple holes 13 may be arranged regularly or irregularly.

In the present embodiment, the shape of the hole 13 may be a polygon other than a rectangle and a square, a circle, an ellipse, or the like in plan view. Also, the shapes and dimensions of the respective holes 13 may not be uniform necessarily.

In the present embodiment, although the through holes 113 and 123 of the patch-type biosensor 100 are formed to have a rectangular shape in plan view, these may be formed to have another shape such as a circle.

In the present embodiment, the patch-type biosensor 100 does not need to be provided with the electronic device 150, the battery 160, or the cover 170.

In the present embodiment, the patch-type biosensor 100 may be provided with a peeling sheet formed of a resin such as polyethylene terephthalate, on the bottom surfaces of the pressure-sensitive adhesive layer 110, the pressure-sensitive adhesive layer 110A, and the probes 140.

EXAMPLES

In the following, the embodiment will be described in further detail with reference to Examples and Comparative examples; note that the embodiment is not limited by these Examples and Comparative examples.

Example 1-1

(Production of Conductive Composition)

As a conductive polymer, 38.0 parts by mass of an aqueous solution containing PEDOT/PSS (PEDOT/PSS by a concentration of 1%, "Clevious PH 1000", manufactured by Heleus); as a binder resin, 10.0 parts by mass of an aqueous solution containing modified polyvinyl alcohol (modified polyvinyl alcohol by a concentration of 10%, "GOSENX Z-410", manufactured by Nippon Synthetic Chemical Co., Ltd.); as a crosslinking agent, 2.0 parts by mass of an aqueous solution containing a zirconium-based compound (a zirconium-based compound by a concentration of 10%, "Safelink SPM-01", manufactured by Nippon Synthetic Chemical Co., Ltd.); as a plasticizing agent, 2.0 parts by mass of glycerin (Wako Pure Chemical Corp.); and as a surfactant, 0.08 parts by mass of a silicone-based surfactant (Silface SAG002, manufactured by Nissin Chemical Co., Ltd.) are added to an ultrasonic bath. Then, the aqueous solution containing these components was mixed in the ultrasonic bath for 30 minutes, to prepare a uniform aqueous solution of the conductive composition.

The concentration of PEDOT/PSS in the aqueous solution containing PEDOT/PSS was approximately 1%; therefore, the content of PEDOT/PSS in the aqueous solution of the conductive composition became 0.38 parts by mass. The concentration of modified polyvinyl alcohol in the aqueous solution containing modified polyvinyl alcohol was approximately 10%; therefore, the content of modified polyvinyl alcohol in the aqueous solution of the conductive composition became 1.00 parts by mass. The concentration of the zirconium-based compound in the aqueous solution containing the zirconium-based compound was approximately 10%; therefore, the content of the zirconium-based compound in the aqueous solution of the conductive composition became 0.20 parts by mass. Note that the remaining parts were the solvent in the aqueous solution of the conductive composition.

The contents of the conductive polymer, the binder resin, the crosslinking agent, the plasticizing agent, and the surfactant with respect to 100 parts by mass of the conductive composition were 10.4 parts by mass, 27.3 parts by mass, 5.5 parts by mass, 54.6 parts by mass, and 2.2 parts by mass, respectively. The ratio (M2/M1) of the content M2 of the plasticizing agent to the content M1 of the conductive polymer was 5.3(=54.6/10.4).

(Production of Electrode)

The prepared aqueous solution of the conductive composition was applied onto a PET film with an applicator, and then, the aqueous solution of the conductive composition was heated and dried at 120° C. for 10 minutes in a drying oven (SPHH-201, manufactured by ESPEC Corp.) to produce a cured material of the conductive composition. Thereafter, the cured material obtained in the dryer was removed from the dryer in a state of closely adhered to the PET film, and pressed by a press machine, to produce an electrode (having the sides being 300 μm long) in which multiple rectangular holes were formed in the principal surface in a mesh.

The content of the conductive polymer and the content of the plasticizing agent in the surface part within a range of 1 μm from the surface of the electrode were measured by using FT-IR. The respective contents of the conductive polymer, the binder resin, the crosslinking agent, the plasticizing agent, and the surfactant were the same as those in the state of the aqueous solution of the conductive composition. In the surface part, the ratio (M2/M1) of the content M2 of the plasticizing agent to the content M1 of the conductive polymer was 13.84.

The composition of the electrode; the ratio (M2/M1) of the content M2 of the plasticizing agent to the content M1 of the conductive polymer; and the ratio (M2/M1) of the content M2 of the plasticizing agent to the content M1 of the conductive polymer in the surface part (0 to 1 μm) are shown in Table 1.

(Evaluation of Modulus of Elongation)

The modulus of elongation of the obtained electrode was measured according to JIS K7161-1:2014. By using a table-top precision universal test machine ("Autograph AGS-50NX", manufactured by Shimadzu Corporation), under conditions of a test temperature set to 23° C.±2° C. and a tensile speed set to 100 mm/min, a tensile test of the electrode was conducted to determine the stress-strain curve. Based on the obtained stress-strain curve, by determining slopes of the curve at two points at which the strains are 0.05% and 0.25%, respectively, the modulus of elongation of the electrode at room temperature (23° C.) was calculated.

In the case where the modulus of elongation was less than or equal to 0.1 GPa, the result was evaluated as good (in Table 1, denoted as A). In the case where the modulus of elongation exceeded 0.1 GPa, the result was evaluated as poor (in Table 1, denoted as B).

Figure 7:
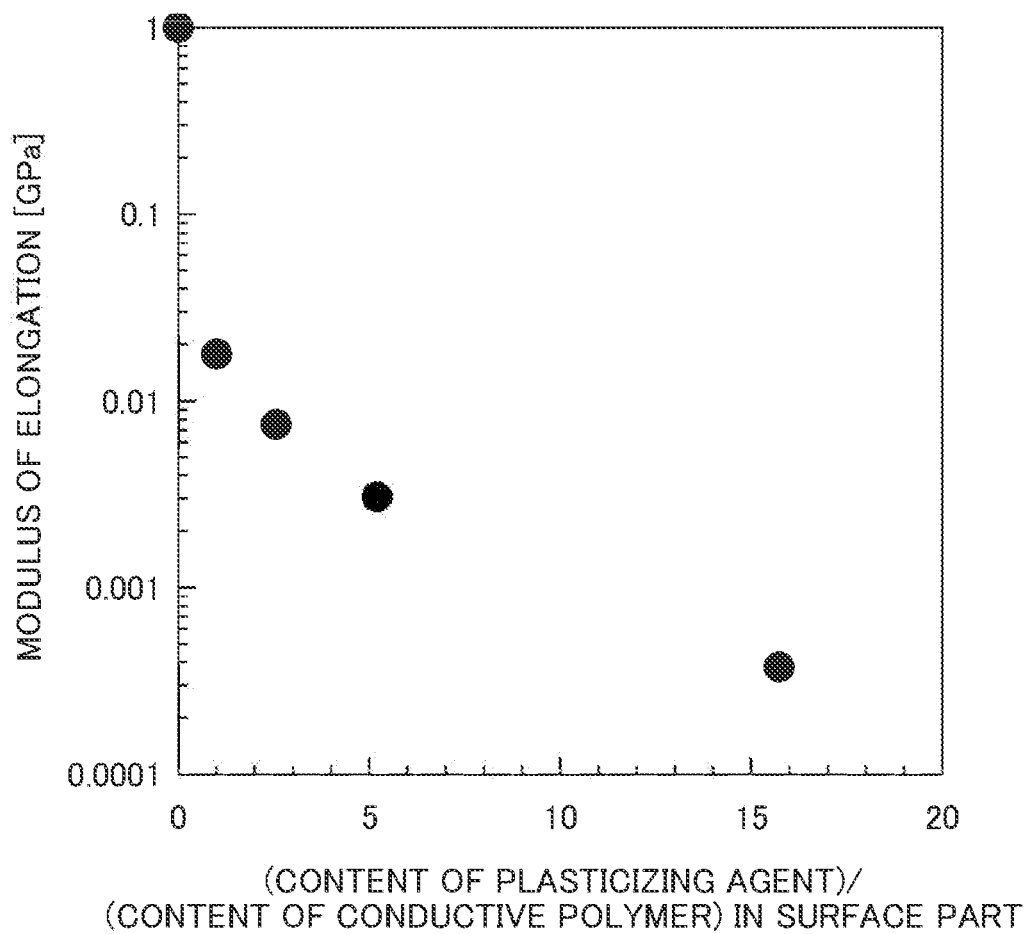
FIG. 7 illustrates a relationship between the ratio of the content of a plasticizing agent to the content of a conductive polymer, and the modulus of elongation.

The measurement results of the modulus of elongation obtained in this way are shown in FIG. 7. Also, the measurement results of the modulus of elongation and the evaluation results are shown in Table 1.

(Evaluation of Handleability)

After having the obtained electrode affixed to a PET film (Lumirror S10, manufactured by Toray Industries, Inc., 50 μm thick), the electrode was evaluated whether it could be peeled off from the PET film. In the case where the electrode could be peeled off from the PET film, the result was evaluated as good (in Table 1, denoted as A), and in the case where the electrode could not be peeled off from the PET film, or the electrode was broken, the result was evaluated as poor (in Table 1, denoted as B).

Example 2

In contrast to Example 1, the content of the plasticizing agent of the conductive composition used for producing the electrodes was set to 10.9 parts by mass, to change the content of the plasticizing agent to approximately ⅕ times that of Example 1, and the ratio (M2/M1) of the content M2 of the plasticizing agent to the content M1 of the conductive polymer was set to 1.0 (=10.9/10.4). In addition, in the surface part of the electrode, the ratio (M2/M1) of the content M2 of the plasticizing agent to the content M1 of the conductive polymer was set to 5.77. Other than these, the production and measurements were performed in substantially the same way as in Example 1.

Example 3

In contrast to Example 1, the content of the plasticizing agent of the conductive composition used for producing the electrodes was set to 27.3 parts by mass, to change the content of the plasticizing agent to approximately ½ times that of Example 1, and the ratio (M2/M1) of the content M2 of the plasticizing agent to the content M1 of the conductive polymer was set to 2.6 (=27.3/10.4); other than these, the production and measurements were performed in substantially the same way as in Example 1.

Example 4

In contrast to Example 1, the content of the plasticizing agent of the conductive composition used for producing the electrodes was set to 163.8 parts by mass, to change the content of the plasticizing agent to approximately 3 times that of Example 1, and the ratio (M2/M1) of the content M2 of the plasticizing agent to the content M1 of the conductive polymer was set to 15.8 (=163.8/10.4). In addition, in the surface part of the electrode, the ratio (M2/M1) of the content M2 of the plasticizing agent to the content M1 of the conductive polymer was set to 320.5. Other than these, the production and measurements were performed in substantially the same way as in Example 1.

Comparative Example 1

In contrast to Example 1, the content of the plasticizing agent of the conductive composition used for producing the electrodes was set to 0.0 parts by mass, to change the content of the plasticizing agent to approximately 0 times that of Example 1, and the ratio (M2/M1) of the content M2 of the plasticizing agent to the content M1 of the conductive polymer was set to 0.0 (=0.0/10.4). In addition, in the surface part of the electrode, the ratio (M2/M1) of the content M2 of the plasticizing agent to the content M1 of the conductive polymer was set to 0.00. Other than these, the production and measurements were performed in substantially the same way as in Example 1.

Comparative Example 2

In contrast to Example 1, the content of the plasticizing agent of the conductive composition used for producing the electrodes was set to 273 parts by mass, to change the content of the plasticizing agent to approximately 5 times that of Example 1, and the ratio (M2/M1) of the content M2 of the plasticizing agent to the content M1 of the conductive polymer was set to 26.25 (=273/10.4); other than these, the production and measurements were performed in substantially the same way as in Example 1.

Table 1 shows the composition of the electrode in the surface part and the modulus of elongation in each of Examples and Comparative examples.

TABLE 1

| | Electrode Composition (parts by mass) | | | | | | Surface part (0~1 μm) | | | | |
|---|---|---|---|---|---|---|---|---|---|---|---|
| | Conductive polymer | Binder resin | Cross-linking agent | Plasticizing agent | Surfactant | Total | (Content of plasticizing agent M2)/(Content of conductive polymer M1) | (Content of plasticizing agent M2)/(Content of conductive polymer M1) | Modulus of elongation Value [GPa] | Modulus of elongation Evaluation | Handleability Evaluation |
| Ex. 1 | 10.4 | 27.3 | 5.5 | 54.6 | 2.2 | 100.0 | 5.3 | 13.84 | 0.003 | A | A |
| Ex. 2 | 10.4 | 27.3 | 5.5 | 10.9 | 2.2 | 56.3 | 1.0 | 5.77 | 0.020 | A | A |
| Ex. 3 | 10.4 | 27.3 | 5.5 | 27.3 | 2.2 | 72.7 | 2.6 | — | 0.008 | A | A |
| Ex. 4 | 10.4 | 27.3 | 5.5 | 163.8 | 2.2 | 209.2 | 15.8 | 320.5 | 0.004 | A | A |
| Comp. ex. 1 | 10.4 | 27.3 | 5.5 | 0.0 | 2.2 | 45.4 | 0.0 | 0.00 | 1.000 | B | B |
| Comp. ex. 2 | 10.4 | 27.3 | 5.5 | 273 | 2.2 | 318.4 | 26.25 | — | — | — | B |

As shown in FIG. 7 and Table 1, in Examples 1 to 4, the modulus of elongation of the electrode was within a range of 0.003 GPa to 0.020 GPa. In contrast, in Comparative example 1, the modulus of elongation of the electrode was 1.0 GPa. Therefore, if M2/M1 in the surface part of the electrode is within a range of 5.77 to 320.5, it was confirmed that the electrode can have a modulus of elongation of 0.003 GPa to 0.020 GPa, and can have a suitable elasticity and a suitable electrical conductivity. Therefore, the electrode according to an embodiment can have stable adhesive strength and electrical conductivity when used as an electrode of a biosensor. Therefore, it can be stated that the biosensor can be effectively used for measuring electrocardiograms continuously for a long period of time (e.g., 24 hours) while being closely adhered to a skin of a test subject.

As above, the embodiments have been described; note that the embodiments are presented by way of example, and the present invention is not limited by the embodiments described above. The embodiments can be implemented in a variety of other forms, and can be combined, omitted, substituted, and altered in various ways within a scope not deviating from the gist of the present invention. These embodiments and variations thereof are included in the scope and gist of the present invention, and included in the scope of the present invention described in the claims and in equivalents thereof.

The present application claims priority under Japanese Patent Application No. 2019-042985 filed with the Japanese Patent Office on Mar. 8, 2019, and the entire contents of Japanese Patent Application No. 2019-042985 are incorporated herein by reference.

DESCRIPTION OF REFERENCE CODES 10 electrode
11,12 principal surface
13,140A hole
100 patch-type biosensor (biosensor)
110 pressure-sensitive adhesive layer
120 base material layer
130 circuit part
140 probe
150 electronic device
160 battery
170 cover

The invention claimed is:

1. An electrode comprising:
a conductive composition containing:
 a conductive polymer;
 a binder resin; and
 a plasticizing agent,
wherein
the electrode has a plate shape, with the plate shape having a pair of principal surfaces parallel to each other,
the conductive polymer is PEDOT/PSS,
the binder resin is a water-soluble polymer,
a content of the conductive polymer is 0.20 to 12 parts by mass with respect to 100 parts by mass of the conductive composition,
a ratio of a content of the plasticizing agent to a content of the conductive polymer in a surface part of the electrode located at less than or equal to 1 μm from at least one principal surface of the pair of the principal surfaces of the electrode is greater than a ratio of a content of the plasticizing agent to a content of the conductive polymer in an entirety of the conductive composition, and
the ratio of the content of the plasticizing agent to the content of the conductive polymer is 0.5 to 350.0 in the surface part of the electrode.

2. The electrode as claimed in claim 1, wherein the electrode has a plurality of holes that penetrate through the electrode in a direction perpendicular to at least one principal surface of the pair of principal surfaces.

3. The electrode as claimed in claim 2, wherein the plurality of holes are arranged in a square lattice pattern, an oblique lattice pattern, or a hexagonal lattice pattern, on the pair of principal surfaces.

4. The electrode as claimed in claim 1, wherein the plasticizing agent is made of glycerin.

5. A biosensor comprising:
the electrode as claimed in claim 1; and
a pressure-sensitive adhesive layer formed on one of the principal surfaces of the electrode.

* * * * *